United States Patent [19]
Bleiweiss et al.

[11] Patent Number: 5,738,873
[45] Date of Patent: Apr. 14, 1998

[54] PHARMACEUTICAL FORMULATIONS AND METHODS FOR TREATING PATIENTS SUFFERING FROM DISEASES THAT CAUSE MUSCULAR HYPOTONIA

[75] Inventors: Herman Bleiweiss, Av. Santa Fe 931, (1059) Buenos Aires; Eduardo Samuel Bleiweiss; Daniel Gustavo Bleiweiss, both of Laprida 1204 7th floor, (1425) Buenos Aires, all of Argentina

[73] Assignees: Herman Bleiweiss; Eduardo Samuel Bleiweiss; Daniel Gustavo Bleiweiss, all of Buenos Aires, Argentina

[21] Appl. No.: 720,354

[22] Filed: Sep. 27, 1996

[51] Int. Cl.$^6$ ..................................................... A61K 9/20
[52] U.S. Cl. ............................................ 424/464; 424/465
[58] Field of Search .................................... 424/464, 465; 514/159; 435/182

[56] References Cited

U.S. PATENT DOCUMENTS 5,470,846  11/1995  Sandyk ..................................... 514/159
5,643,773  7/1997  Aebischer et al. ........................ 435/182

*Primary Examiner*—Thurman K. Page
*Assistant Examiner*—William E. Benston, Jr.
*Attorney, Agent, or Firm*—Evelyn M. Sommer

[57] ABSTRACT

Formulations are provided for the treatment of patients suffering from disorders that have in common the appearance of muscular hypotonia as a symptom. These disorders include Alzheimer's type diseases, atrophy of the brain, atrophy of the cerebellum, Fragile X syndrome, mental retardation of unknown causes, multiple anomalies in the chromosomes, deletions in one or more chromosome, and fragility in a chromosome other than the X chromosome. The formulations of the invention contain therapeutically effective amounts of gamma amino butyric acid (GABA), an anti-oxidant (such as ascorbic acid and/or vitamin E), folic acid, nicotinamide, and a lithium salt, all in a pharmaceutically acceptable excipient. Methods for the treatment of these disorders by the administration of such formulations are also provided.

12 Claims, No Drawings

PHARMACEUTICAL FORMULATIONS AND METHODS FOR TREATING PATIENTS SUFFERING FROM DISEASES THAT CAUSE MUSCULAR HYPOTONIA

FIELD OF THE INVENTION

The present invention relates to the treatment of a variety of disorders which have in common the symptom of muscular hypotonia. More specifically, the invention pertains to the pharmaceutical treatment of such disorders, using a formulation of neurotransmitters, antioxidants, vitamins, and a lithium salt.

BACKGROUND OF THE INVENTION

The present invention is directed to the treatment of a variety of seemingly unrelated disorders, for which no fully satisfactory treatment is currently available.

One of these is Fragile X syndrome, a chromosomal abnormality which causes mental retardation. Some children, especially girls, can carry the fragile X chromosome without developing any symptoms, which suggests that fragile X syndrome may be amenable to external influences. Some have suggested that this also creates a hope that the retardation might respond to pharmaceutical treatment. *Genetics of Neuropsychiatric diseases*, Lennart, Ed., Wetterburg 1988, Macmillan Press, Ltd., p. 117.

Indeed, some drug therapies for fragile X syndrome have been tried. For example, in 1982, Lejeune proposed the use of folic acid; but controlled studies failed to show any improvement of the mental coefficient of the patients treated. Stimulating drugs were used by Gustavson and his colleagues in 1985, but the results were only significant when considered on a case-by-case basis. Unfortunately, there have been no reports of further success in the pharmaceutical treatment of fragile X syndrome.

There are also a number of other mental disorders which may be amenable to pharmaceutical treatment, but for which no satisfactory treatment has been found. For example, mental retardation arising from various causes, and also the senile dementias such as Alzheimer's disease, also can be treated using drugs of various sorts. Unfortunately, no such drug treatments are very satisfactory, and proving the effectiveness of drugs in the treatment of dementias can be quite difficult. *Handbook of Dementing Illnesses*, John C. Morris, Ed., Marcel Dekker 1994, p. 591. Part of this difficulty arises from the fact that it can often be difficult to clearly diagnose what type of dementia a patient has.

The above-described mental disorders often present severe symptoms of retardation and/or dementia, which are often accompanied by psychosis. In such cases, strong psychotropic agents such as the prescription neuroleptic drugs may be of benefit. However, there are also patients in which the symptoms are much less severe, yet where pharmaceutical treatment may still offer the prospect of some symptomatic relief. Such patients are often hyperkinetic, or may suffer from poor concentration. For these reasons they may fail to learn, and may become delayed in the development of social behavior. In other cases, where patients that are in the early stages of a dementing illness, symptoms are often not severe, with the most notable problem being a mild loss of memory or vocabulary.

The above-described disorders all have one thing in common: they all tend to cause muscular hypotonia. Unfortunately, the existence of this common symptomatology has thus far not resulted in the development of any drug treatments that might benefit all patients who suffer from these otherwise disparate diseases. Were there such a common therapy, mistakes in the difficult task of diagnosing specific disorders would not lead to the use of inappropriate therapies, which unfortunately often is the case.

SUMMARY OF THE INVENTION

The overall objective of the present invention, then, is to provide compositions and methods for the pharmaceutical treatment of fragile X syndrome, retardation of various causes, and also the dementias such Alzheimer's disease. The present invention is most useful for the treatment of such disorders in cases where psychotic symptoms do not appear, and where the use of prescription neuroleptic drugs would not be indicated.

Importantly, because of the difficulty often encountered in diagnosing what specific type of retardation or dementia a patient has, a further object of the present invention is to provide a single therapy that can be of benefit in all such disorders, such that the use of the present therapy would have therapeutic value even if the patient's disorder has been misdiagnosed within the general group. This is much preferable to the more usual case, where misdiagnosis can lead to the selection of a therapy that is inappropriate, and of little or no therapeutic value to the treatment of the disease that the patient actually has.

One embodiment of the present invention is a pharmaceutical formulation comprising non-toxic amounts of the following components in a pharmaceutically acceptable excipient:

a) gamma amino butyric acid (GABA);

b) antioxidants selected from the group consisiting of ascorbic acid, vitamin E and mixtures thereof;

c) folic acid;

d) nicotinamide or an pharmaceutically acceptable salt thereof; and e) a lithium salt.

In one preferred embodiment, the following non-toxic amounts of the components are used:

a) about 0.05 to about 200 mg of gamma amino butyric acid (GABA);

b) about 50 to about 300 mg of an antioxidant selected from the group consisting of vitamin E, ascorbic acid and mixtures of same;

c) about 100 to about 300 mg of folic acid;

d) about 0.05 to about 0.5 mg of nicotinamide or a pharmaceutical salt of same; and e) about 25 to about 100 mg of a lithium salt selected from the group consisting of lithium carbonate, lithium chloride, lithium bromide, or lithium acetate.

In another preferred embodiment, the following non-toxic amounts of the components are used:

a. about 0.100 mg of gamma amino butyric acid (GABA);

b. about 200 mg of an antioxidant selected from the group consisting of ascorbic acids vitamin E and mixtures of same;

c. about 200 mg of folic acid;

d. about 0.100 mg of nicotinamide; and e. about 50 mg of lithium carbonate.

In a most preferred embodiment, the following non-toxic amounts of the components are used:

a. 100 mg of gamma amino butyric acid (GABA);

b. an antioxidant comprising about 150 mg vitamin E plus about 0.5 mg of ascorbic acid;

c. about 200 mg of folic acid;

a) about 0.1 mg of nicotinamide; and b) about 50 mg of lithium carbonate.

The present invention also relates to methods for treating the above-described disorders. One such method comprises administering to a patient therapeutically effective daily dosages of the following components:

a. gamma amino butyric acid (GABA);

b. an anti-oxidant selected from the group of ascorbic acid, vitamin E, and mixtures thereof;

c. folic acid;

d. nicotinamide; and e. a lithium salt.

A preferred method is the administration of the following therapeutically effective daily dosages to a patient:

a. about 0.05 to about 200 mg of gamma amino butyric acid (GABA);

b. about 50 to about 300 mg of an antioxidant selected from the group consisting of vitamin E, ascorbic acid, and mixtures thereof;

c. about 100 to about 300 mg of folic acid;

d. about 0.05 to about 0.5 mg of a nicotinamide amide selected from the group consisting of nicotinamide and pharmaceutically acceptable salts thereof;

e. about 25 to about 100 mg of a lithium salt selected from the group consisting of lithium carbonate, lithium bromide, lithium chloride, and lithium acetate.

Another preferred method is the administration of the following therapeutically effective daily dosages to a patient:

a. about 0.100 mg of gamma amino burytic acid (GABA);

b. about 200 mg of an antioxidant selected from the group of ascorbic acid, vitamin E and mixtures thereof;

c. about 200 mg of folic acid;

d. about 0.1 mg of nicotinamide;

e. about 50 mg of lithium carbonate.

Yet another preferred method is the administration of the following therapeutically effective daily dosages to a patient:

a. about 50 mg to about 400 mg of gama amino butyric acid (GABA);

b. about 75 to 600 mg of the antioxidant vitamin E and about 0.25 to 2.0 mg of the antioxidant ascorbic acid;

c. about 100 mg to about 800 mg of folic acid;

d. about 0.05 mg to about 0.4 mg of nicotinamide; and e. about 25 mg to about 200 mg of lithium carbonate.

A most preferred method comprises administering daily to a patient about one half (½) to about four (4) dosage units, each such dosage unit comprising, in a pharmaceutically acceptable excipient:

a. 100 mg of gamma amino butyric acid (GABA);

b. an antioxidant comprising about 150 mg vitamin E plus about 0.5 mg of ascorbic acid;

c. about 200 mg of folic acid;

c) about 0.1 mg of nicotinamide; and d) about 50 mg of lithium carbonate.

DETAILED DESCRIPTION OF THE INVENTION

The disorders which are the subject of the present application appear to have widely varying symptoms. However, through the observation, study and treatment of patients suffering from Alzheimer's Disease and other dementias, chromosomal anomalies such as deletions and fragility, and those suffering from other pathologies which are mentioned elsewhere herein, the applicant has observed that these diseases have a common symptom, muscular hypotonia. This is often accompanied by lessened states of consciousness, and both of these symptoms can become progressively worse with time. Applicant believes that these disorders also share certain alterations in the levels of certain neurotransmitters.

These pathological conditions can be acquired or inherited, and their appearance and progression can vary according to age, sex, and the patient's state of health. Without treatment, this type of pathology evolves unfavorably, with a progressive deterioration of the cognitive, communication, and social abilities of the affected patients.

In the course of the observation, study and comparison of these patients, including those who had been subjected, without success, to different conventional treatments, the applicant was able to observe perceptible improvements in patients treated with a unique mixture of pharmacological agents which can be best described as neurotransmitters, vitamins and a lithium salt. These improvements, which are described in the examples below, appear to have resulted from synergistic effects of the agents used in combination. These and other experimental treatments have led the applicant to formulate the pharmaceutical formulations described herein.

The compounds used in making the formulations described herein may be used in any of the various chemical forms that are commonly known in the art. Most preferred forms are the base compounds alone, and pharmaceutically acceptable salts thereof.

The individual compounds which comprise the formulations of the present invention are well known in the art, and detailed explanations are thus not needed. For example, gamma amino butyric acid (GABA) and its salts are well known in the field of neurochemistry, most notably because of their anti-arrhythmic effects. The anti oxidants ascorbic acid (or ascorbates) and vitamin E are well known free-radical scavengers, which serve to inhibit the oxidizing effects of $O_2$ by terminating the oxidation chain reactions that are believed to play an important role in the aging process. The ascorbic acid used can also be in the form of sodium ascorbate, or can alternatively be combined with nicotinamide (component 1) in the form of ascorbic nicotinamide. Nicotinamide is an important component of nicotinamide adenine dinucleotide, or NAD, and its reduced form, NADH, which are coenzymes that are quite important in oxidative phosphorylation. Lithium is an element which is widely recognized as having therapeutic value in the treatment of manic states, most notably the mania that occurs in patients suffering from manic-depressive syndrome. Folic acid is a coenzyme which has a variety of roles in cellular metabolism, including a role as coenzyme in the synthesis of nucleosides.

The present invention relates generally to the administration of these agents simultaneously, which the applicant has found to provide a benefit substantially greater than would be expected from the effects of the individual agents when given alone.

The present invention, in its broadest embodiment, is a formulation comprising gamma amino butyric acid; an antioxidant selected from the group consisting of ascorbic acid, vitamin E and mixtures thereof; folic acid; nicotinamide or a pharmaceutically acceptable salt of nicotinamide; a lithium salt; and a pharmaceutically acceptable excipient. The present invention also comprises methods of treating patients using such formulations.

Of course, in preparing the formulations of the present invention, pharmaceutically recognized equivalents of each of the components (e.g., salts) and conjugates of same (e.g., ascorbic nicotinamide) can alternatively be used. Moreover, although it is preferable to administer all of the agents in a single dosage form, this is not necessary; each of the components can be administered to the patient in separate dosage units, or they can, for example, be combined such that each dosage unit contains two or more of the components. In addition, although it is preferable to do so, it is not necessary that all of the components be taken at the same time. It is only necessary that they all be taken each day of therapy. The administration of the several compoments thus can be spread out throughout the day, if desired.

A variety of oral dosage forms can be used, including tablets, pills, powders, coated pills, water capsules, elixirs, suspensions, emulsions, solutions, and syrups. The formulations of the present invention can be prepared by mixing the active ingredients with an excipient, by dissolving them and then diluting them with an excipient, or by mixing the ingredients with an excipient and introducing them in a carrier such as a capsule or ampoule. Other dosage forms and methods of preparation will be readily apparent to those of ordinary skill in the art, and these would be within the scope of the present invention as well.

The excipients used in preparing the formulations of the present invention can be of solid, semi solid or liquid material. The primary purpose of the excipient is to act as a vehicle for the active ingredients. Some examples of suitable excipients are lactose, dextrose, saccharose, sorbitol, mannitol, starches, gum arabic, calcium phosphate, algins, tragacanth, gelatin, calcium silicate, micro-crystalline cellulose, polyvinylpyrrolidone, cellose, water, syrup, and methyl cellulose. The formulations can also optionally contain lubricating agents such as talcum powder, magnesium stearate and mineral oil; humectant agents, emoluments and suspending agents; preservatives such as methyl and propyl hydroxybenzoate; and sweeteners or flavoring agents. Of course, there are a myriad of other ingredients that could be added, as will be appreciated by those of skill in the art. The compounds of this invention can also be formulated for rapid, sustained or extended release of the active ingredients, using a variety of coatings, matrices, delivery devices, and other drug delivery mechanisms that are well known in the field.

The present invention is illustrated by the examples set forth below. Of course, it is not intended that these examples limit the scope of the present invention, as those of ordinary skill in the art can formulate alternative embodiments which would also be well within the scope of the present invention.

EXAMPLE 1

Patients were first studied through a thorough evaluation of family history, patient history, and symptoms, as well as through the use of a variety of diagnostic tests, all of which are well known in the art. All patients also underwent a psychiatric interview, and where Alzheimer's type diseases or other atrophy in the central nervous system was suspected, a computed axial tomography (CAT) scan of the brain was carried out, and cerebral mapping was performed. In addition, a battery of neurometabolic tests were performed, including the measurement of urine levels of adrenaline, noradrenalin, dopamine, phenyl acetic acid, dimethyltryptamine and phenylethylamine. In cases of where retarded maturity was evident, a chromosomal evaluation was performed, and a psychological study was made, in order to establish each patient's mental coefficient.

Based upon the results of this analysis, patients were each assigned to one or more of the following groups:

1) Patients with an Alzheimer's type disease;

2) Patients with atrophy in the brain or the cerebellum;

3) Patients with Fragile X syndrome;

4) Patients with an unspecified retarded maturity;

5) Patients with numeric anomalies in their chromosomes;

6) Patients with a deletion in one or more chromosome; and

7) Patients with fragility in a chromosome other than the X chromosome.

In the examples that follow, patients falling within each of these groups were treated with capsules containing the following ingredients, along with an excipient (hereinafter referred to as the "Test Formulation"):

GABA, 100 mg.

vitamin E, 150 mg.

ascorbic acid, 0.5 mg.

folic Acid, 200 mg.

nicotinamide, 0.1 mg.

lithium Carbonate, 50 mg.

Patients were treated as described in the further examples below. Treatment was only begun upon the consent of the relatives of the patient, and those relatives were also kept informed throughout the duration of the study. As further described below, treatment with the Test Formulation produced positive results in about 60% of patients with Alzheimer's type diseases, about 90% of the patients with Fragile X Syndrome, and about 72% of patients with unspecified retarded maturity.

EXAMPLE 2

For patients diagnosed as falling into classes 1 and 2, that is, suffering from an Alzheimer's type of disease or atrophy of the brain or the cerebellum, the administration of the Test Formulation was continued over a period of 10 weeks; each patient was observed, and each patient's family was asked about his behavior, at intervals of 25 days.

The overall result was that patients with Alzheimer's type diseases showed improvement in their speech, and in their ability to recognize things and persons. Some of them regained control of their bladders and rectal sphincters, thus overcoming their prior incontinence and making their care considerably easier. Some patients even became able to carry out household chores. Specific results with individual patients are described below.

A.E, male, 78 years old

In November 1991 he started to experience a loss of memory; he would forget people's names, fail to recognize places, and also forget trips that he had taken to other countries. He was initially treated with cyanaricine. When diazepam was added as part of his treatment, he got confused and could not even recognize his house. His neurometabolic levels were: adrenaline, 25 mg (normal range, 1–20 mg); noradrenaline, 10 mg (normal range, 15–80 mg); dopamine, 42 mg (normal range, 65–400 mg); dimethyltryptamine, 0.25 mg (normal range, <0.05 mg); phenylethylamine, 9 mg (normal range, 6–12 mg); phenylacetic acid, 159 mg (normal range, 100–200 mg). The CAT scan showed involution of the cortex and frontal lobe.

A.E. was given a Test Formulation capsule three times each day. After 3 months of treatment his memory improved, and he began to watch T.V. In general, he became better socially related. After 2 years of treatment, his improvement still continues.

L. C. L., male, 80 years old

L. C. L. is a lawyer who about 8 years ago he began to experience memory loss, and to develop abnormal personality traits. His CAT scan showed that there was cerebral atrophy, and an EEG taken in December of 1991 showed an abnormally high number of theta waves. In hope of improving the circulation in his brain, he was initially treated with nicardipine, 20 mg daily, piritinol, 200 mg daily, and carbamazepine 100 mg daily. When 1 ½ capsules of the Test Formulation per day was added to his treatment regimen, his ability to use language improved considerably, as did his sense of humor and his memory. He uses many new words, his vocabulary is enriched, he remembers everyday facts, and he remembers episodes of his life.

F. B. R., female, 68 years old

F. B. R. was a skiing instructor who four years ago started to experience memory loss. This memory loss progressed to the point that she could not recognize her family. She was diagnosed as having Alzheimer's disease, and her family sought treatment in Rome, Vienna, Budapest, and other places around the world, but there was no improvement. A CAT scan showed generalized cortical atrophy. She was treated with four capsules of the Test Formulation daily, and she showed substantial improvement in her speech, her vocabulary, her ability to walk, her ability to recognize people, and her ability to enjoy operas. She can even remember actors and music.

C. D. J. O., female, 73 years old

In 1989 this patient was diagnosed as having Alzheimer's disease, primarily on the basis of her memory loss, and because her CAT scan showed that there had been cerebral atrophy. She initially was treated with imipramine; 25 mg daily, fluphenazine, 0.5 mg daily, and nortriptyline, 10 mg twice daily; but this medication provided no improvement. The various neurometabolic tests that were performed, as described above, showed all levels to be within normal ranges.

After receiving two capsules of the Test Formulation per day, her sleep patterns and social skills both markedly improved.

EXAMPLE 3

Patients in class 3, who have Fragile X syndrome, were treated with the Test Formulation for 4 months; they were observed, and their families were asked about their behavior, at one month intervals. As illustrated by the individual cases described below, an improvement was observed in 90% of the patients studied. Moreover, improvement was clearly significant in the cognitive area: patients who had previously been unable to do so began to speak, read and write.

L. M. A., female, 14 years old

This patient suffered from learning difficulties, and a karyotype showed that 16% of the chromosomes displayed fragile X. She had a short attention span, made rough movements, and expressed herself in a childish way. Her Intelligence quotient ("IQ") was 60. Her neurometabolic levels were noradrenaline 30.8 mg (normal range, 15–80 mg); adrenaline 13.7 mg (normal range, 1–20 mg); dopamine 163, 1 mg (normal range, 65–400 mg); phenylacetic acid, 107 mg (normal range, 100–200 mg); phenylethylamine, 18 mg (normal range, 6–12 mg).

With different previous treatments, including the use of carbamazepine, this patient had seen no change. But when she received three capsules of the Test Formulation daily, she improved noticeably. Her learning abilities improved and her attention span increased.

F. I. D., male, 10 years old

This patient's karyotype showed 5% fragile X cells. He did not have convulsions, but his IQ was only 54. With different treatments, including include $B_{12}$, he did not improve. However, after receiving 4 capsules of the Test Formulation daily, his school performance improved, and his social behavior was better. He also was able to begin to read and write. Everyone at school, at home, and those on our medical team, including the applicant, were able to verify this improvement.

EXAMPLE 4

The following patients fell within groups 4–8; they had mental retardation of unknown cause, multiple anomalies in their chromosomes, deletions in one or more chromosome, or fragility in a chromosome other than the X chromosome. Those with mental retardation of unknown cause were treated with the Test Formulation for a period of two months, with monthly observations and inquiries of their families regarding any changes they may have observed. Those with the chromosomal abnormalities listed above were treated for four months; their families were asked about their behavior every month, and the patient was also observed by the applicant every month. Overall, improvement was seen in about 70% of the patients treated.

B. C. G., female, 16 years old

When she first started school, her parents and teacher noted that she was having difficulties in learning. By the age of 16, she still had not learned to read and write. However, she was not aggressive and did not suffer from convulsions.

B. C. G.'s EEG showed bioelectrical instability, and her karyotype showed that she had a constitution of 46, XX;inv (9)p11q13, but that she was fragile X negative. Her IQ was only 69. The neurometabolic study showed the following levels: adrenaline, 9 mg (normal range, 1–20 mg); noradrenaline, 5 mg (normal range, 15–80 mg) dopamine 60 mg (normal range, 65–400 mg); dimethyltryptamine, 0.26 mg (normal range, <0.5 mg); phenylethylamine 8.3 mg (normal range, 6–12 mg); and phenylacetic acid, 94 mg (normal range, 100–200 mg).

This patient had previously received several different treatments, including folic acid, Vit. $B_{12}$ and $B_1$, but there had been no improvement. However, after 2 months of treatment with one tablet of the Test Formula per day, she began to improve. At the present, she performs better at school, is more independent and more socialized. Her vocabulary is richer, she answers to questions and has a good sense of humor.

I. J. L., female, 12 years old

This patient suffered from considerable developmental delay: she did not speak until after 16 months of life, and she was not successfully toilet trained until age 3. She appeared to be hyperactive and to have poor concentration skills. She had previously been treated with folic acid and vitamin $B_{12}$, but there had been no detectable improvement.

After being treated with one capsule of the Test Formulation per day, she clearly had improved; she appeared to be interested in things more so than before, and she began to ask many more questions than she did before. But the way she asked the questions was most important, in that she used complete phrases and expressed clear ideas.

We claim:

1. A pharmaceutical formulation for the treatment of a disorder having muscular hypotonia as a symptom, selected from the group of an Alzheimer's disease, atrophy of the brain, atrophy of the cerebellum, Fragile X syndrome, mental retardation of unknown causes, multiple anomalies in the chromosomes, deletion in one or more chromosome, and fragility in a chromosome other than the X chromosome, said formulation comprising non toxic quantities of the following components in a pharmaceutically acceptable excipient:

a. about 0.05 to about 200 mg of gamma amino burytic acid (GABA);

b. about 50 to about 300 mg of an antioxidant selected from the group consisting of vitamin E, ascorbic acid, and mixtures thereof;

c. about 100 to about 300 mg of folic acid;

d. about 0.05 to about 0–5 mg of a nicotinamide selected from the group consisting of nicotinamide and pharmaceutically acceptable salts thereof; and e. about 25 to about 100 mg of a lithium salt selected from the group consisting of lithium carbonate, lithium bromide, lithium chloride, and lithium acetate.

2. The pharmaceutical formulation of claim 1 wherein said antioxidant and said nicotinamide are present as ascorbate nicotinamide.

3. The pharmaceutical formulation of claim 1 wherein said formulation is further processed into a dosage form selected from the group consisting of tablets, pills, powders, coated pills, water capsules, elixirs, suspensions, emulsions, solutions, and syrups.

4. The formulation of claim 1 wherein said excipient is selected from the group consisting of lactose, dextrose, saccharose, sorbitol, mannitol, starches, gum arabic, calcium phosphate, algins, tragacanth, gelatin, calcium silicate, micro-crystalline cellulose, polyvinylpyrrolidone, cellose, water, syrup, methyl cellulose, and mixtures of any of the forgoing.

5. The formulation of claim 1 further comprising one or more agents selected from the group consisting of lubricating, humectant, emulgent, and suspending agents.

6. The formulation of claim 1 further comprising a lubricating agent selected from the group consisting of talcum powder, magnesium stearate and mineral oil.

7. The pharmaceutical formulation of claim 1 wherein said non-toxic quantities of said components are:

a. about 100 mg of gama amino butyric acid (GABA);

b. antioxidant, comprising a mixture of about 150 mg of vitamin E and about 0.5 mg of ascorbic acid;

c. about 200 mg of folic acid;

d. about 0.1 mg of nicotinamide; and e. about 50 mg of lithium carbonate.

8. The pharmaceutical formulation of claim 1 wherein said non-toxic quantities of said components are:

a. about 0.100 mg of gamma amino butyric acid;

b. about 200 mg of an antioxidant selected from the group of ascorbic acid, vitamin E and mixtures thereof;

c. about 200 mg of folic acid;

d. about 0.1 mg of nicotinamide; and e. about 50 mg of lithium carbonate.

9. A method for the treatment of a patient suffering from a disorder having muscular hypotonia as a symptom, said disorder selected from the group of an Alzheimer's disease, atrophy of the brain, atrophy of the cerebellum, Fragile X syndrome, mental retardation of unknown causes, multiple anomalies in the chromosomes, deletion in one or more chromosome, and fragility in a chromosome other than the X chromosome, said method comprising administering daily to said patient about one half (½) to about four (4) dosage units of the pharmaceutical formulation of claim 7.

10. The method of claim 1, wherein said therapeutically effective daily dosages are:

a. about 0.100 mg of gamma amino butyric acid;

b. about 200 mg of an antioxidant selected from the group of ascorbic acid, vitamin E and mixtures thereof;

c. about 200 mg of folic acid;

d. about 0.1 mg of nicotinamide;

e. about 50 mg of lithium carbonate.

11. A method for the treatment of a patient suffering from a disorder having muscular hypotonia as a symptom, said disorder selected from the group of an Alzheimer's disease, atrophy of the brain, atrophy of the cerebellum, Fragile X syndrome, mental retardation of unknown causes, multiple anomalies in the chromosomes, deletion in one or more chromosome, and fragility in a chromosome other than the X chromosome, said method comprising administering to said patient therapeutically effective daily dosages of the following components:

a. about 0.05 to about 200 mg of gamma amino burytic acid (GABA);

b. about 50 to about 300 mg of an antioxidant selected from the group consisting of vitamin E, ascorbic acid, and mixtures thereof;

c. about 100 to about 300 mg of folic acid;

d. about 0.05 to about 0.5 mg of a nicotinamide selected from the group consisting of nicotinimide and pharmaceutically acceptable salts thereof;

e. about 25 to about 100 mg of a lithium salt selected from the group consisting of lithium carbonate, lithium bromide, lithium chloride, and lithium acetate.

12. A method for the treatment of a patient suffering from a disorder having muscular hypotonia as a symptom, said disorder selected from the group of an Alzheimer's disease, atrophy of the brain, atrophy of the cerebellum, Fragile X syndrome, mental retardation of unknown causes, multiple anomalies in the chromosomes, deletion in one or more chromosome, and fragility in a chromosome other than the X chromosome said method comprising administering to said patient therapeutically effective daily dosages of the following components:

about 50 to about 400 mg of gamma amino burytic acid (GABA);

b. about 75 to about 600 mg of the antioxidant vitamin E and about 0.25 to 2.0 mg of the antioxidant ascorbic acid;

c. about 100 to about 800 mg of folic acid;

d. about 0.05 to about 0°4 mg of nicotinamide;

e. about 25 to about 100 mg of lithium carbonate.

* * * * *